United States Patent
Chung et al.

(10) Patent No.: US 9,295,629 B2
(45) Date of Patent: Mar. 29, 2016

(54) WNT FAMILY-DERIVED PEPTIDES AND USE THEREOF

(75) Inventors: Yong Ji Chung, Yongin-si (KR); Eun Mi Kim, Gunpo-si (KR)

(73) Assignee: CAREGEN CO., LTD., Gunpo-si, Gyeonggi-do (KR)

( * ) Notice: Subject to any disclaimer, the term of this patent is extended or adjusted under 35 U.S.C. 154(b) by 0 days.

(21) Appl. No.: 14/236,504

(22) PCT Filed: May 9, 2012

(86) PCT No.: PCT/KR2012/003638
§ 371 (c)(1),
(2), (4) Date: Apr. 30, 2014

(87) PCT Pub. No.: WO2013/018976
PCT Pub. Date: Feb. 7, 2013

(65) Prior Publication Data
US 2014/0309157 A1   Oct. 16, 2014

(30) Foreign Application Priority Data

Aug. 4, 2011   (KR) .......................... 10-2011-0077566

(51) Int. Cl.
| | | |
|---|---|---|
| *A61K 38/00* | (2006.01) | |
| *A61K 38/18* | (2006.01) | |
| *A61K 8/64* | (2006.01) | |
| *C07K 14/71* | (2006.01) | |
| *C07K 7/06* | (2006.01) | |
| *C07K 7/08* | (2006.01) | |
| *A61Q 19/00* | (2006.01) | |
| *A61Q 5/00* | (2006.01) | |
| *A61Q 19/08* | (2006.01) | |
| *A61Q 7/00* | (2006.01) | |

(52) U.S. Cl.
CPC ... *A61K 8/64* (2013.01); *A61Q 5/00* (2013.01); *A61Q 7/00* (2013.01); *A61Q 19/00* (2013.01); *A61Q 19/08* (2013.01); *C07K 7/06* (2013.01); *C07K 7/08* (2013.01); *C07K 14/71* (2013.01); *A61K 38/00* (2013.01)

(58) Field of Classification Search
CPC ......... A61K 38/00; A61K 38/18; A61K 8/64; C07K 14/71; C07K 7/06; C07K 7/08
USPC ......... 514/18.6, 18.8, 1.2, 20.7; 530/327, 328
See application file for complete search history.

(56) References Cited

U.S. PATENT DOCUMENTS

| | | | | |
|---|---|---|---|---|
| 4,966,848 | A * | 10/1990 | Smith et al. | .................... 435/193 |
| 5,223,421 | A * | 6/1993 | Smith et al. | .................... 435/193 |
| 5,837,218 | A * | 11/1998 | Peers et al. | .................... 424/1.69 |
| 2002/0114772 | A1 | 8/2002 | Morgan et al. | |
| 2004/0247593 | A1* | 12/2004 | He et al. | ..................... 424/143.1 |
| 2006/0115460 | A1 | 6/2006 | Naughton | |
| 2013/0045209 | A1* | 2/2013 | Gurney | ....................... 424/139.1 |

FOREIGN PATENT DOCUMENTS

| | | | |
|---|---|---|---|
| EP | 2474555 A1 | 7/2012 | |
| KR | 10-2011-0023991 A | 3/2011 | |
| WO | WO 00/61630 | * 10/2000 | ............ C07K 14/475 |

OTHER PUBLICATIONS

Harris JM, Chess RB, "Effects of Pegylation on Pharmaceuticals," Nature, Mar. 2003, vol. 2, 214-221.*
International Search Report for International Application No. PCT/KR2012/003638, dated Nov. 13, 2012 (7 pages).

* cited by examiner

*Primary Examiner* — Julie Ha
(74) *Attorney, Agent, or Firm* — Clark & Elbing LLP; Susan M. Michaud

(57) ABSTRACT

A WNT-derived peptide and use thereof are described. WNT-derived peptide of the present invention possesses identical or similar activities to natural-occurring WNT protein, and has much higher stability and skin penetration potency than natural-occurring WNT protein. Therefore, the composition containing the present peptide not only shows excellent effects on improvement in hair loss (for example, promotion of hair growth or production of hair), but also has superior efficacies on treatment of a WNT signal transduction pathway-related disorder. In addition, the outstanding activity and stability of the present peptide described above may be greatly advantageous in application to pharmaceutical compositions, quasi-drugs and cosmetics.

11 Claims, 15 Drawing Sheets

1: Control  2: Peptide −1  3: Peptide −2
4: Peptide −3  5: Peptide −4

Peptide concentration : 1 μg/mℓ

1: Control  2: Peptide -1  3: Peptide -2
4: Peptide -3  5: Peptide -4

Peptide concentration : 1 μg/ml

1: Control  2: DKK-1  3: DKK-1+Peptide -1  4: DKK-1+Peptide-2
5: DKK-1+Peptide -3  6: DKK-1+Peptide -4

Peptide concentration : 1 μg/ml
DKK-1 concentration : 10 ng/ml

SEQUENCE LISTING

<160> NUMBER OF SEQ ID NOS: 4

<210> SEQ ID NO 1
<211> LENGTH: 12
<212> TYPE: PRT
<213> ORGANISM: Artificial Sequence
<220> FEATURE:
<223> OTHER INFORMATION: WNT-derived peptide 1

<400> SEQUENCE: 1

Leu Cys Cys Gly Arg Gly His Arg Thr Arg Thr Gln
1               5                   10

<210> SEQ ID NO 2
<211> LENGTH: 10
<212> TYPE: PRT
<213> ORGANISM: Artificial Sequence
<220> FEATURE:
<223> OTHER INFORMATION: WNT-derived peptide 2

<400> SEQUENCE: 2

Leu Cys Cys Gly Arg Gly His Asn Ala Arg
1               5                   10

<210> SEQ ID NO 3
<211> LENGTH: 10
<212> TYPE: PRT
<213> ORGANISM: Artificial Sequence
<220> FEATURE:
<223> OTHER INFORMATION: WNT-derived peptide 3

<400> SEQUENCE: 3

Ala Glu Arg Arg Arg Glu Leu Cys Arg Cys
1               5                   10

<210> SEQ ID NO 4
<211> LENGTH: 10
<212> TYPE: PRT
<213> ORGANISM: Artificial Sequence
<220> FEATURE:
<223> OTHER INFORMATION: WNT-derived peptide 4

<400> SEQUENCE: 4

Leu Cys Cys Gly Arg Gly His Asn Val Leu
1               5                   10

WNT FAMILY-DERIVED PEPTIDES AND USE THEREOF

CROSS-REFERENCE TO RELATED APPLICATIONS

This application is the U.S. national stage filing under 35 U.S.C. §371 of PCT International Application PCT/KR2012/003638, filed May 9, 2012, which claims priority from KR Patent Application 10-2011-0077566, filed Aug. 4, 2011.

BACKGROUND OF THE INVENTION

1. Field of the Invention

The present invention relates to a WNT family-derived peptide and use thereof.

2. Description of the Related Art

Hair follicle is a peculiar skin organ of mammals, which is developed from the bottom of primitive epidermis into much internal skin layer. The plug of cells known as follicle or dermal papilla exists in the base of the hair follicle (Stenn and Paus, *Physiol. Rev.*, 81: 449 (2002)), and papilla is essential in normal circulation of the hair follicle (Oliver, *Embryol. Exp. Morph.* 15: 331 (1966); Oliver, *Embryol. Exp. Morph.* 16: 231 (1967)) and in growth of the hair shaft. The hair shaft is a thread-shaped epithelial cells that are composed of keratin filaments and filament-aggregating proteins tightly attached thereto.

Human hair follows a growth cycle with three distinct phases: anagen, catagen, and telogen phases. The hair growth cycle is regulated by hormones or many growth factors. Severe stress or malnutrition may advance the catagen and telogen phases, leading to severe hair loss (alopecia) (Vladimir A. Botchkarev, *American Journal of Pathology*, 162 (3): 709-712 (2003)). In male pattern baldness, the hair follicles at the front and top of the scalp are sensitive to androgen, which causes the follicles to miniaturize, thereby resulting in hair loss. Briefly, excessive secretion of androgen activates 5-α reductase which causes testosterone to be converted to dihydrotestosterone (DHT). Subsequently, DHT reduces the number of thick dark terminal hairs by shortening a period of hair growth and by miniaturing hair follicles, leading to hair loss. It has been supposed that about 20% of hair loss women suffer from a few disorders called as "female pattern baldness" which the hair often becomes thinner at the top of the scalp. In addition, hair loss broadens with aging. For example, severe hair loss may be caused from different disorders such as cicatricial alopecia or scar conditions including burns or compression injury. Whatever is the cause, while woman power in the workforce has been enhanced and men have cared about their appearance, hair loss may have remarkable psychological, social and sexual impacts as well as loss of pride and self-respect. Although various medicaments have been used to treat hair loss, they are too expensive or give very different adverse effects among individuals. Additionally, it is necessary to take these drugs in a constant manner. In this connection, it is one of serious drawbacks that hair loss may be caused by stopping them. Meanwhile, another demerit is that their efficacies and side effects may be quietly different between individuals.

Therefore, the development of cheaper and more effective novel active ingredient is needed in this industrial field.

Raw materials utilized in cosmetic products have the advantage of being inexpensive, whereas do not give good results since they are composed of plant extract-derived components. It has been known up to now that two commercial drugs (minoxidil and finasteride) may delay only additional hair loss. However, no actual medicaments may have been useful to induce regeneration of new hair follicle in practice. Many scalp cosmetics for preventing hair loss have been commercially available in the market, for example including: (a) a product including a plant extract derived from sophora, hot pepper, Swertia herb, *Morus alba*, mulberry leaf, *ginseng*, licorice, peony, foxglove, fennel, Japanese cornel, garlic, and so forth; (b) a composition containing xanthines and growth hormones for not only improving cellular metabolism suppressed by excess dihydrotestosterone (DHT) but also facilitating hair growth through hair loss inhibition and hair regeneration induced by growth hormones; (c) a product containing minerals, vitamins and extracts of green tea, rosemary, mugwort or licorice, which supplies nutrients to the scalp and hair for preventing hair loss and promoting hair growth; and (d) a male pattern baldness product mixing the substances such as vitamin B, vitamin C, vitamin D, vitamin E, nicotinic acid, pantothenic acid, biotin, folic acid, etc. with plant extracts, which inhibits 5-α reductases to suppress production of DHT during androgen metabolism and to help hair metabolism by have been developed. However, they have hardly influence on the production of new hair. As another example, a research group of the Jikei University School of Medicine in Tokyo, Japan has developed the product using corosolic acid known to be effective in diabetes, which inhibits 5-α reductases and exhibits an excellent effect on hair growth.

Many factors are associated with each other in the growth and degeneration of hair. For hair production, the present researchers have studied serial growth factors having an activity for: (a) promoting proliferation of keratinocyte which is most important for hair root production; (b) inducing differentiation of hair; (c) supplying nutrients to the vicinity of hair; and (d) activating vascular endothelial growth factors.

Of them, human-derived WNT specifically affects hair development by transferring a signal to a cell. WNT signal transduction pathway is activated by an interaction between secreted WNT protein and Frizzled protein which is a receptor thereof. In this connection, LDL receptor-related proteins (LRP5 and LRP6) function as a co-receptor (Clin Cancer Res 2007; 13 (14) Jul. 15, 2007, WNT Signaling Pathway and Stem Cell Signaling Network). Downstream effects in WNT signal transduction pathway include participation of Axin-β-catenin-GSK3 β complex through activation of DVL (Disheveled) protein and Akt (Fukumoto et al., *J. Biol. Chem.*, 276: 17479-17483 (2001)). Afterwards, GSK3 β is inactivated by phosphorylation, resulting in inhibition of phosphorylation and degradation of β-catenin. Accumulated β-catenins are translocated to a nucleus and then interact with transcription factors of the lymphoid enhancer factor-T cell factor (LEF-TCF), permitting to induce transcription of target genes. The resulting proteins may be a critical role for hair growth and differentiation, and allow new hair cell to be produced. Furthermore, they decrease activities of DHT produced by male hormone (androgen) to suppress hair loss.

Throughout this application, various patents and publications are referenced and citations are provided in parentheses. The disclosure of these patents and publications in their entities are hereby incorporated by references into this application in order to more fully describe this invention and the state of the art to which this invention pertains.

DETAILED DESCRIPTION OF THIS INVENTION

For developing peptides having actions identical to natural-occurring human WNT protein as well as having more enhanced activity, stability and skin penetration than natural-occurring WNT protein, the present inventors have made intensive researches. As a result, the present inventors have discovered several WNT related peptides having excellent characteristics described above on the basis of the amino acid sequence of natural-occurring WNT protein, eventually accomplishing the present invention.

Accordingly, it is one object of this invention to provide a peptide essentially consisting of an amino acid sequence selected from the group consisting of amino acid sequences of SEQ ID NO:1, SEQ ID NO:2, SEQ ID NO:3, and SEQ ID NO:4.

It is another object of this invention to provide a composition for promoting hair growth or improving hair production containing the aforementioned peptide of this invention as an active ingredient.

It is still another object of this invention to provide a composition for improving hair loss containing the aforementioned peptide of this invention as an active ingredient.

It is still another object of this invention to provide a composition for improving skin conditions containing the aforementioned peptide of this invention as an active ingredient.

It is still another object of this invention to provide a composition for improving or treating a WNT signal transduction pathway-related disorder containing the aforementioned peptide of this invention as an active ingredient.

It is further still another object of this invention to provide a composition for treating a DKK-1 protein (an antagonist of WNT signaling pathway)-induced disorder.

Other objects and advantages of the present invention will become apparent from the following detailed description together with the appended claims and drawings.

In one aspect of this invention, there is provided a peptide essentially consisting of an amino acid sequence selected from the group consisting of amino add sequences of SEQ ID NO:1, SEQ ID NO:2, SEQ ID NO:3, and SEQ ID NO:4.

For developing peptides having actions identical to natural-occurring human WNT protein as well as having more enhanced activity, stability and skin penetration than natural-occurring WNT protein, the present inventors have made intensive researches. As a result, the present inventors have discovered several WNT related peptides having excellent characteristics described above on the basis of the amino acid sequence of natural-occurring WNT protein, eventually accomplishing the present invention.

The peptide of the present invention derived from human WNT protein and comprises an amino acid sequence selected from the group consisting of amino acid sequences from SEQ ID NO:1 (peptide 1) to SEQ ID NO:4 (peptide 2). Preferably, the peptide in this invention essentially consists of an amino acid sequence selected from the group consisting of amino acid sequences from SEQ ID NO:1 to SEQ ID NO:4. The term used herein "peptide" refers to a linear molecule formed by linking between amino acid residues through peptide bonds.

The peptides of the present invention may be prepared by conventional chemical synthesis processes known to one of skill in the art, in particular, solid-phase synthesis techniques (Merrifield, *J. Amer. Chem. Soc.* 85: 2149-54 (1963); Stewart, et al., *Solid Phase Peptide Synthesis,* 2nd. ed., Pierce Chem. Co.: Rockford, 111 (1984)).

The peptides of the present invention may be prepared by primarily predicting a portion of capable of binding to a receptor protein through random partial synthesis of several portions in WNT protein and then optimizing an amino acid sequence of the predicted portion. Afterwards, the candidate peptides having the most excellent activity are screened to isolate the peptides of this invention.

The peptide of SEQ ID NO:1 (peptide-1), SEQ ID NO:2 (peptide-2), SEQ ID NO:3 (peptide-3), or SEQ ID NO:4 (peptide-4) not only has actions similar to natural-occurring WNT protein but also shows growth factor activities via binding to a receptor.

The peptides of this invention per se have higher stability than natural-occurring WNT protein.

According to a preferable embodiment, the peptides of this invention have at their N-terminal a protection group selected from the group consisting of acetyl group, fluorenyl methoxy carbonyl group, formyl group, palmitoyl group, myristyl group, stearyl group and polyethylene glycol (PEG).

The modifications of peptides described above greatly increase the stability of the peptides of this invention. The term used herein "stability" refers to in vivo stability and storage stability (e.g., storage stability at room temperature) as well. The protection group described above protects the peptides from the attack of protease in vivo.

In another aspect of this invention, there is provided a composition for promoting hair growth or improving hair production containing the peptide of this invention as an active ingredient.

In still another aspect of this invention, there is provided a method for promoting hair growth or improving hair production comprising administering to a subject the peptide of this invention.

In further still another aspect of this invention, there is provided a use of the peptide of this invention for manufacturing a medicament to promote hair growth and improve hair production.

Since the present composition comprises the growth factor-related peptides of this invention as active ingredients described above, the common descriptions between them are omitted in order to avoid undue redundancy leading to the complexity of this specification.

As demonstrated in Examples below, the growth factor-related peptides of the present invention have stimulatory activity to cell proliferation in keratinocytes, fibroblasts or hair follicles and follow β-catenin signaling as a representative signal pathway of WNT protein. It could be verified that the peptide of the present invention allows WNT signal pathway to be active in spite of the presence of DKK-1 as a WNT inhibitor. In addition, fibronectin expression as a target gene of WNT was enhanced by the present peptide. Furthermore, it could be demonstrated that the peptide of the present invention contributes to enhanced fibronectin expression even in the presence of DKK-1. According to animal experiments based on the above-mentioned results, it could be appreciated that the peptide of the present invention significantly promotes hair growth.

In another aspect of this invention, there is provided a composition for improving hair loss containing the peptide of this invention as an active ingredient.

In still another aspect of this invention, there is provided a method for improving hair loss comprising administering to a subject the peptide of this invention.

In further still another aspect of this invention, there is provided a use of the peptide of this invention for manufacturing a medicament to improve hair loss.

The peptide of this invention induces the proliferation and differentiation of stem cells in hair follicles of the skin and further allows them to migrate into hair root and to become new follicles. In addition, the peptide of this invention is able to enhance the expression of gene which stimulates hair production through the activation of β-catenin signaling even in the condition that WNT signaling is inhibited by the presence of hair-loss stimulating DKK-1 (Dickkopf-1) gene, whose expression has been induced by DHT (dihydrostestosterone). Furthermore, the peptide of this invention has a function of promoting the growth phase of hair cycle, in which hair generates and grows, and prohibits hair growth cycle from entrance into telogen phase which is induced by various environmental unfavorable factors. Through the actions above mentioned, the peptide of this invention has the function of preventing hair loss, stimulating hair growth and providing healthy fair with more nutrition. Accordingly, the composition of the present invention is very effective in hair growth and improvement of skin conditions.

In another aspect of this invention, there is provided a composition for improving skin conditions containing the peptide of this invention as an active ingredient.

In still another aspect of this invention, there is provided a method for improving skin conditions comprising administering to a subject the peptide of this invention.

In further still another aspect of this invention, there is provided a use of the peptide of this invention for manufacturing a medicament to improve skin conditions.

According to a preferable embodiment, the improvement in the skin conditions by the present peptide is improvement in wrinkle or skin elasticity, prevention of skin aging, improvement in skin moisture, removal of wound or regeneration of skin.

In another aspect of this invention, there is provided a composition for preventing or treating a WNT signal transduction pathway-related disorder, containing the peptide of this invention as an active ingredient.

In still another aspect of this invention, there is provided a method for preventing or treating a WNT signal transduction pathway-related disorder, comprising administering to a subject the peptide of this invention.

In further still another aspect of this invention, there is provided a use of the peptide of this invention for manufacturing a medicament to prevent or treat a WNT signal transduction pathway-related disorder.

According to a preferable embodiment, the WNT signal transduction pathway-related disorder includes a bone disorder, a disease associated with bone development, a bone fracture, a senile bone loss, chondrodystrophia, hypercalcemia, hyperostosis, osteogenesis imperfect, osteomalacia, osteomyelitis, osteoporosis, Paget's disease of bone, osteoarthritis, rachitis or obesity. More preferably, the WNT signal transduction pathway-related disorder includes osteoporosis, bone disease or obesity.

In another aspect of this invention, there is provided a composition for preventing or treating a DKK-1 protein (an antagonist of WNT signaling pathway)-related disorder, containing the peptide of this invention as an active ingredient.

In still another aspect of this invention, there is provided a method for preventing or treating a DKK-1 protein (an antagonist of WNT signaling pathway)-related disorder, comprising administering to a subject the peptide of this invention.

In further still another aspect of this invention, there is provided a use of the peptide of this invention for manufacturing a medicament to prevent or treat a DKK-1 protein (an antagonist of WNT signaling pathway)-related disorder.

According to a preferable embodiment, the DKK-1 protein-related disorder includes insulin resistance, hypoinsulinemia, hyperinsulinemia, diabetes or obesity.

According to a preferable embodiment, the composition is a pharmaceutical composition containing: (a) a pharmaceutically effective amount of the growth factor-related peptide of the present invention; and (b) a pharmaceutically acceptable carrier.

The term used herein "pharmaceutically effective amount" refers to an amount enough to show and accomplish efficacies and activities of the growth factor-related peptide of this invention.

The pharmaceutically acceptable carrier contained in the pharmaceutical composition of the present invention, which is commonly used in pharmaceutical formulations, but is not limited to, includes lactose, dextrose, sucrose, sorbitol, mannitol, starch, rubber arable, potassium phosphate, arginate, gelatin, potassium silicate, microcrystalline cellulose, polyvinylpyrrolidone, cellulose, water, syrups, methylcellulose, methylhydroxy benzoate, propylhydroxy benzoate, talc, magnesium stearate, and mineral oils. The pharmaceutical composition according to the present invention may further include a lubricant, a humectant, a sweetener, a flavoring agent, an emulsifier, a suspending agent, and a preservative. Details of suitable pharmaceutically acceptable carriers and formulations can be found in *Remington's Pharmaceutical Sciences* (19th ed., 1995), which is incorporated herein by reference.

The pharmaceutical composition according to the present invention may be administered orally or parenterally, and preferably, administered parenterally, e.g., by intravenous, subcutaneous, intramuscular, intraperitoneal, local or transdermal administration.

A suitable dosage amount of the pharmaceutical composition of the present invention may vary depending on pharmaceutical formulation methods, administration methods, the patient's age, body weight, sex, pathogenic state, diet, administration time, administration route, an excretion rate and sensitivity for a used pharmaceutical composition. Preferably, the pharmaceutical composition of the present invention may be administered with a daily dosage of 0.001-1000 mg/kg.

According to the conventional techniques known to those skilled in the art, the pharmaceutical composition according to the present invention may be formulated with pharmaceutically acceptable carrier and/or vehicle as described above, finally providing several forms a unit dose form and a multi-dose form. Non-limiting examples of the formulations include, but not limited to, a solution, a suspension or an emulsion in oil or aqueous medium, an extract, an elixir, a powder, a granule, a tablet and a capsule, and may further comprise a dispersion agent or a stabilizer.

According to a preferable embodiment, the composition is a cosmetic composition containing: (a) a cosmetically effective amount of the growth factor-related peptide of the present invention; and (b) a cosmetically acceptable carrier.

The term used herein "cosmetically effective amount" refers to an amount enough to accomplish efficacies on improvements in skin conditions described hereinabove.

The cosmetic compositions of this invention may be formulated in a wide variety of forms, for example, including a solution, a suspension, an emulsion, a paste, an ointment, a gel, a cream, a lotion, a powder, a soap, a surfactant-containing cleanser, an oil, a powder foundation, an emulsion foundation, a wax foundation and a spray. Specifically, the cosmetic compositions of this invention may be formulated in the form of skin softener, nutrient liquid, nutrient cream, massage cream, essence, eye cream, cleansing cream, cleansing foam, cleansing water, pack, spray or powder.

Where the cosmetic composition is in the form of paste, cream or gel, it may include animal and vegetable fats, waxes, paraffins, starch, tragacanth, cellulose derivatives, polyethylene glycols, silicones, bentonites, silica, talc, zinc oxide or mixtures of these substances.

In the formulation of powder or spray, it may include lactose, talc, silica, aluminum hydroxide, calcium silicate, polyamide powder and mixtures of these substances. Spray may additionally comprise the customary propellants, for example, chlorofluorohydrocarbons, propane/butane or dimethyl ether.

The formulation of solution and emulsion may include solvent, solubilizer and emulsifier, for example water, ethanol, isopropanol, ethyl carbonate, ethyl acetate, benzyl alcohol, benzyl benzoate, propylene glycol, 1,3-butylglycol, oils, glycerol fatty esters, polyethylene glycol and fatty acid esters of sorbitan.

The formulation of suspension may contain liquid diluents, for example water, ethanol or propylene glycol, suspending agents, for example ethoxylated isostearyl alcohols, polyoxyethylene sorbitol esters and poly oxyethylene sorbitan esters, microcrystalline cellulose, aluminum metahydroxide, bentonite, agar and tragacanth or mixtures of these substances.

The formulation of cleansing compositions with surfactant may contain aliphatic alcohol sulfate, aliphatic alcohol ether sulfate, sulfosucinnate monoester, isothinate, imidazolium derivatives, methyltaurate, sarcocinate, fatty acid amide ether sulfate, alkyl amido betain, aliphatic alcohol, fatty acid glyceride, fatty acid diethanolamide, vegetable oil, lanoline derivatives, ethoxylated glycerol fatty acid ester or mixtures of these ingredients.

Furthermore, the cosmetic compositions of this invention may contain auxiliaries as well as peptides as active ingredients and carriers. The non-limiting examples of auxiliaries include preservatives, antioxidants, stabilizers, solubilizers, vitamins, colorants, odor improvers or mixtures of these substances.

The features and advantages of the present invention will be summarized as follows:

(i) WNT-derived peptide of the present invention possesses identical or similar activities to natural-occurring WNT;

(ii) the peptides of the present invention have much higher stability and skin penetration potency than natural-occurring WNT;

(iii) therefore, the composition containing the present peptide not only shows excellent effects on improvement in hair loss (for example, promotion of hair growth or production of hair), but also has superior efficacies on treatment of a WNT signal transduction pathway-related disorder; and (iv) the outstanding activity and stability of the present peptide described above may be greatly advantageous in application to pharmaceutical compositions, quasi-drugs and cosmetics.

The present invention will now be described in further detail by examples. It would be obvious to those skilled in the art that these examples are intended to be more concretely illustrative and the scope of the present invention as set forth in the appended claims is not limited to or by the examples.

EXAMPLES

Preparation Example 1

Figure 1:
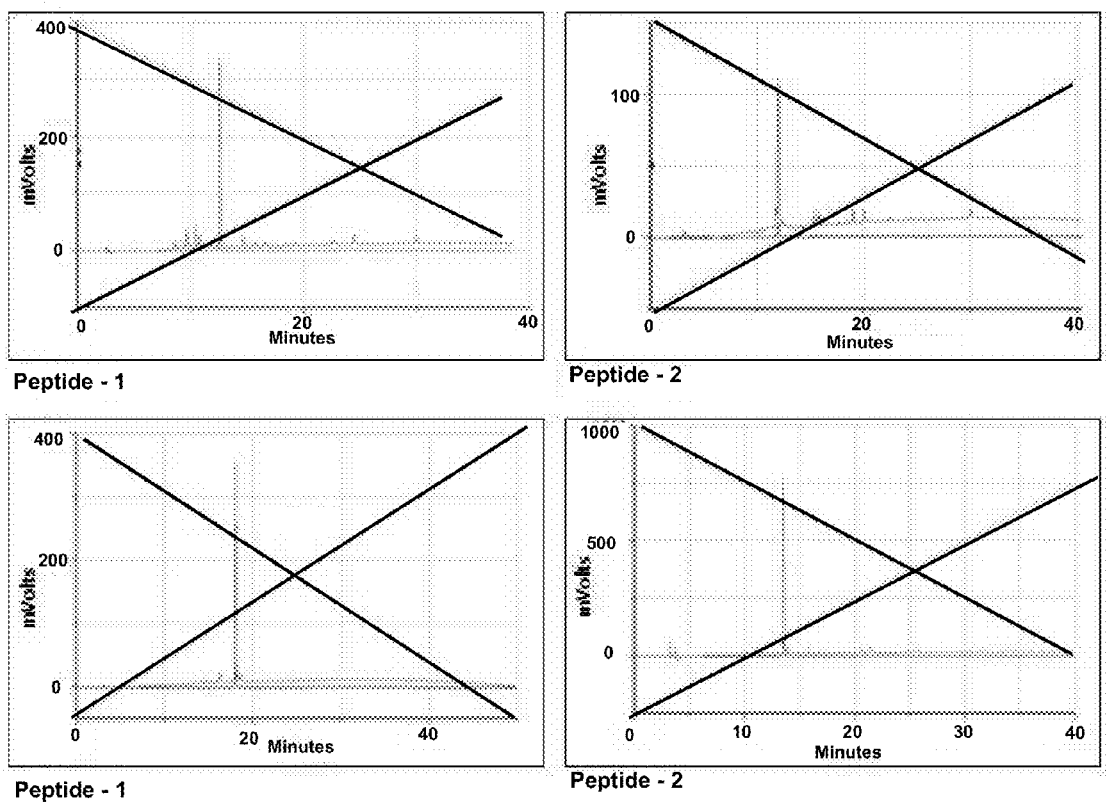
FIG. 1 represents results of HPLC (high performance liquid chromatography) analysis of the peptides of SEQ ID NO:1 (peptide-1), SEQ ID NO:2 (peptide-2), SEQ ID NO:3 (peptide-3), and SEQ ID NO:4 (peptide-4) prepared in Preparation Example.

Synthesis of Leu-Cys-Cys-Gly-Arg-Gly-His-Arg-Thr-Arg-Thr-Gln-Arg (SEQ ID NO:1) and Other Peptides 700 mg of chloro trityl chloride resin (CTL resin, Nova Biochem Cat No. 01-64-0021) were introduced into a reactor, to which 10 ml of methylene chloride (MC) were added, followed by agitation for 3 min. After removing solution, 10 ml of dimethylformamide (DMF) were added to the resultant and then agitation was carried out for 3 min, after which the solvent was removed. 10 ml of dichloromethane solution were added to the reactor and 200 mmole of Fmoc-Arg(pbf)-OH (Bachem, Swiss) and 400 mmole of DIEA (N,N'-diisopropyl ethylamine) were then added to the reactor, after which the mixture was dissolved by agitation and reaction was then undertaken with agitating for 1 hr. After washing, methanol and DIEA (2:1) dissolved in DCM (dichloromethane) were reacted with the resin for 10 min, and then the resultant was washed using excess of DCM/DMF (1:1). After removing the solution, 10 ml of DMF were added to the resultant and agitation was performed for 3 min, followed by removing the solvent. 10 ml of a deprotection solution (20% piperidine/DMF) were added to the reactor and agitated for 10 min at room temperature, followed by removing the solution. After adding the same volume of the deprotection solution, the reaction was undertaken for 10 min and solution was removed, followed by washing sequentially with DMF (3 times), MC (1 times) and DMF (1 times) to yield Arg(pbf)-CTL resins. 10 ml of DMF solution was added to a new reactor and then 200 mmole of Fmoc-Gln(trt)-OH (Bachem, Swiss), 200 mmole of HoBt and 200 mmole of Bop were added, followed by agitation for solubilization. 400 mmole of DIEA was added to the reactor twice as a fraction and agitation was carried out for at least 5 min to dissolve all solid contents. The dissolved amino acids solution was introduced into the reactor containing the deprotected resin and reaction was undertaken with agitating for 1 hr at room temperature. Following the removal of the reaction solution, the resultant was agitated three times (each for 5 min) with DMF solution to remove unreacted residuals. A small amount of the reacted resin was taken to evaluate extent of reactions by Ninhydrine test. Using the deprotection solution, the deprotection was performed twice in the same manner as described above to yield Gln(trt)-Arg(pbf)-CTL resin. After washing with DMF and MC, further Ninhydrine test was carried out and the sequential attachments of amino acids below were performed as described above. Based on the amino acid sequence designed by the present inventors, Fmoc-Thr(tBu), Fmoc-Arg(pbf), Fmoc-Thr(tBu), Fmoc-Arg(pbf), Fmoc-His(trt), Fmoc-Gly, Fmoc-Arg(pbf), Fmoc-Gly, Fmoc-Cys, Fmoc-Cys, and Fmoc-Leu were sequentially attached to resins. Fmoc-protecting group was removed by thoroughly incubating with the deprotection solution twice for 10 min. For acetylation, acetic anhydride, DIEA and HoBt were incubated with the peptidyl resins for 1 hr. The prepared peptidyl resins were washed three times with DMF, MC and methanol, respectively, and gradually dried under nitrogen atmosphere, after which it was completely vacuum-dried under $P_2O_5$. The dried resins were reacted with 30 ml of a leaving solution [containing 95% trifluroacetic acid (TFA), 2.5% distilled water, 2.5% thioanisole] for 2 hr at room temperature upon intermittent agitating. The resin was filtered and washed with a small volume of TFA solution, after which the filtrate was combined with the mother liquor. After distillation under reduced pressure to reduce the total volume by two, the precipitation was induced using 50 ml of cold ether and the formed precipitates were collected by centrifugation, followed by washing twice with cold ether. After removing the mother liquor, the resultant was completely dried under nitrogen atmosphere to yield 0.65 g of unpurified peptide 1, Leu-Cys-Cys-Gly-Arg-Gly-His-Arg-Thr-Arg-Thr-Gln-Arg (yield rate; 92.6%). The molecular weight of the final product was determined as 1543.8 (theoretical MW: 1543.81) using a mass analyzer. The other peptides of SEQ ID NO:2, SEQ ID NO:3, and SEQ ID NO:4 were also synthesized by the process described in the above (FIG. 1).

TABLE 1

| SEQ ID NO | Amino acid sequence | Analyzed values (mass analyzer) | |
|---|---|---|---|
| | | Analyzed values | Theoretical values |
| 1 (Peptide-1) | LCCGRGHRTRTQR | 1240.4 | 1239.5 |
| 2 (Peptide-2) | LCCGRGHNAR | 1447.6 | 1446.5 |
| 3 (Peptide-3) | AERRRELCRC | 1240.4 | 1239.5 |
| 4 (Peptide-4) | LCCGRGHNVL | 1447.6 | 1446.5 |

Experimental Example 1

Influence of Peptides on Cell Growth

In order to evaluate three peptides prepared in Preparation Examples 1-2 whether they have similar activities of growth factor, SRB (Sulforhodamine B; Sigma-Aldrich) colorimetric assay was carried out using HaCaT kerationcytes (Korean Cell Line Bank) and NIH3T3 fibroblasts (Korean Cell Line Bank) according to Rizzino et al. method (Rizzino, et al. *Cancer Res.*, 48: 4266 (1988)).

HaCaT ketatinocytes, NIH3T3 fibroblasts, and HHFDPC hair follicle cells (cell science) were cultured in 250 ml-flasks containing DMEM (Dulbecco's Modified Eagle's minimal essential media; Gibco, USA) supplemented with 10% FBS (fetal bovine serum; Sigma). Cells cultured were treated with 1% trypsin solution to detach cells from the bottom of culture flasks and centrifuged to collect cell pellets. After cells were resuspended in DMEM not containing FBS, its aliquot ($3 \times 10^3$ cells) was added to each well of 96-well plates and cultured under 5% $CO_2$ for 24 hr at 37° C. After 24-hr culture, the medium was changed with a fresh medium without serum and cells were incubated with empty sample (for normalization) and peptides synthesized (1 ng/ml, 10 ng/ml, 100 ng/ml, 1 μg/ml and 10 μg/ml) aseptically dissolved in 10% DMSO for 72 hr under the same conditions as described above. After removing supernatants, cells were fixed with ethanol and then washed three times using PBS (phosphate buffered saline), followed by incubation with SRB solution. Cells were sufficiently washed with 1% acetic acid and observed under a microscope to find living cell condition. In addition, absorbance at 590 nm was measured to analyze cell viability. Meanwhile, after culturing under the same conditions, the tissue was immunostained by an immunohistochemical assay with ki-67 antibody (SantaCruz, USA) and the amount of ki-67 protein as a cell proliferation marker was observed.

Figure 2A:
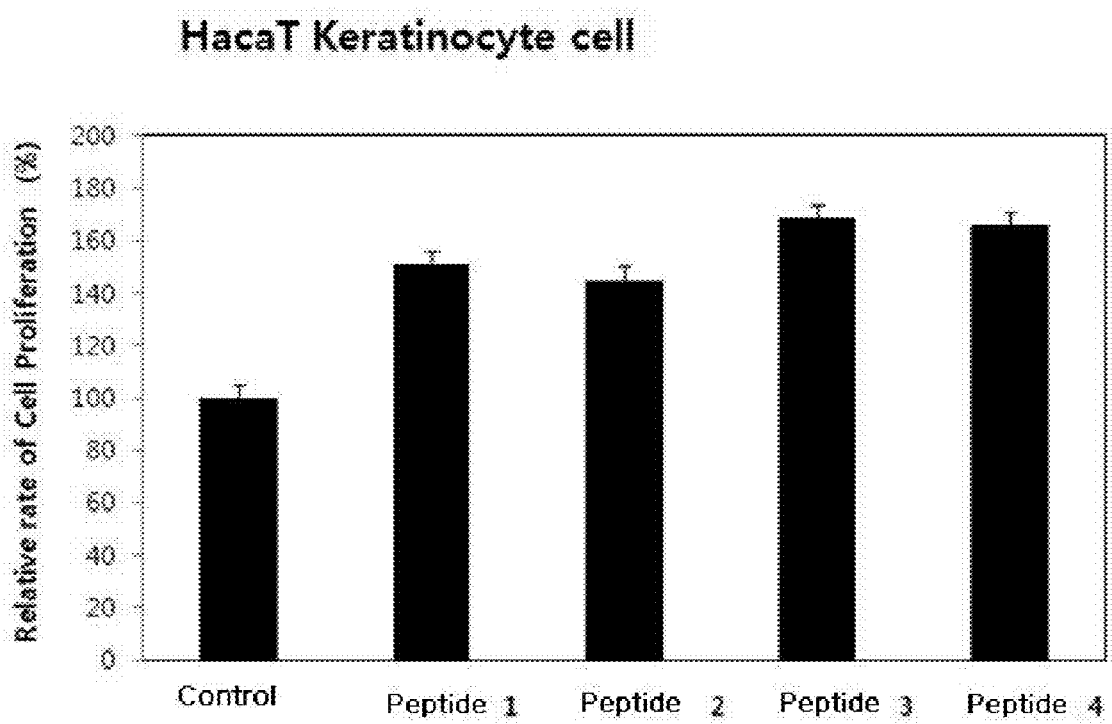
FIG. 2a is a graph representing a stimulatory effect on the growth of keratinocytes treated with the peptides of SEQ ID NO:1 (peptide-1), SEQ ID NO:2 (peptide-2), SEQ ID NO:3 (peptide-3), and SEQ ID NO:4 (peptide-4) prepared in Preparation Example.
Figure 2B:
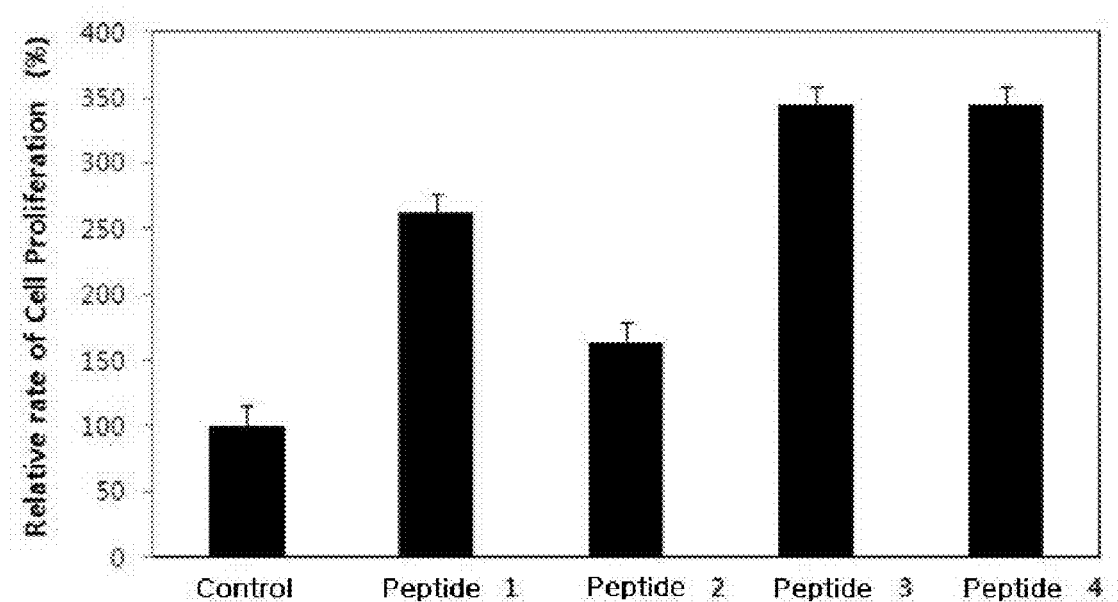
FIG. 2b is a graph representing a stimulatory effect on the growth of fibroblasts treated with the peptides of SEQ ID NO:1 (peptide-1), SEQ ID NO:2 (peptide-2), SEQ ID NO:3 (peptide-3), and SEQ ID NO:4 (peptide-4) prepared in Preparation Example.
Figure 2C:
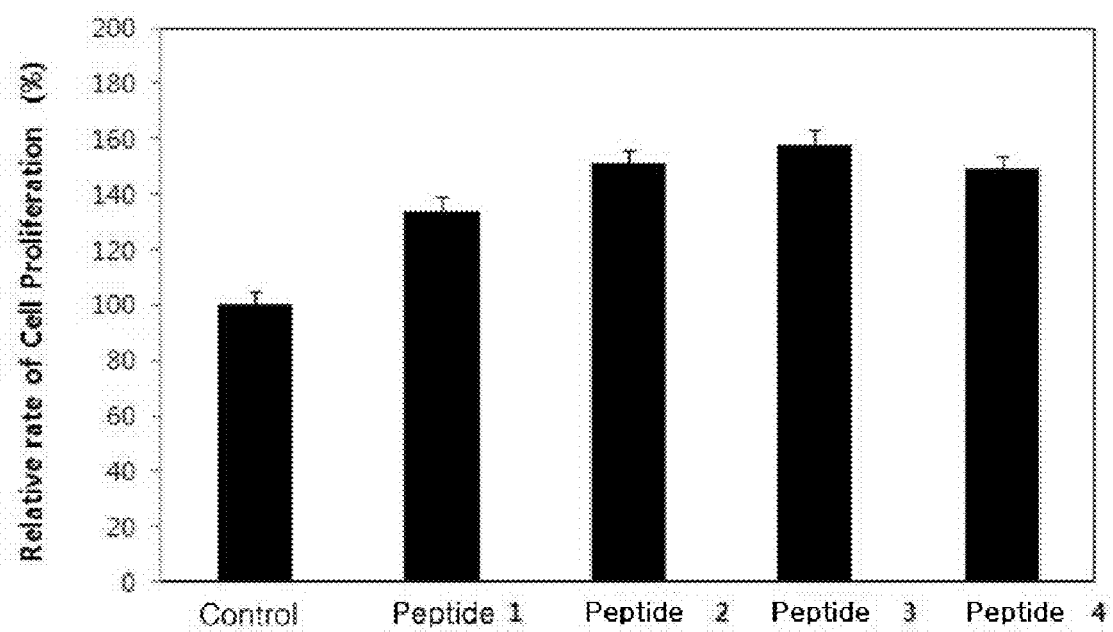
FIG. 2c is a graph representing a stimulatory effect on the growth of cells in hair follicles treated with the peptides of SEQ ID NO:1 (peptide-1), SEQ ID NO:2 (peptide-2), SEQ ID NO:3 (peptide-3), and SEQ ID NO:4 (peptide-4) prepared in Preparation Example.
Figure 3A:
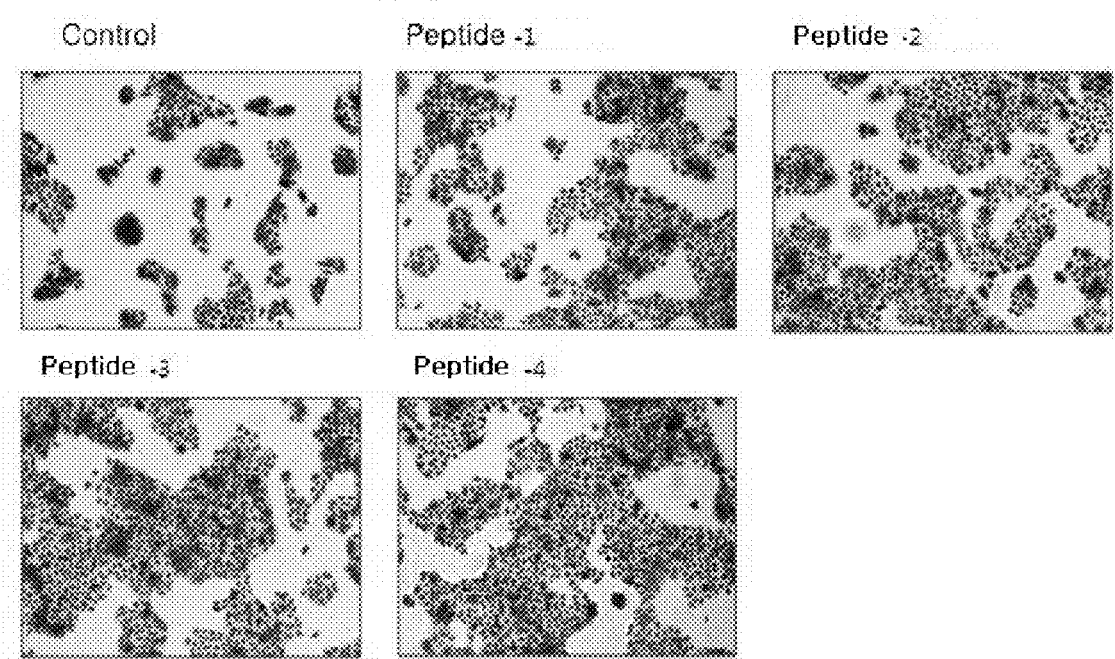
FIG. 3a is a microscope image demonstrating effects of the peptides of the present invention [SEQ ID NO:1 (peptide-1), SEQ ID NO:2 (peptide-2), SEQ ID NO:3 (peptide-3), and SEQ ID NO:4 (peptide-4)] to promote the growth of keratinocytes.
Figure 3B:
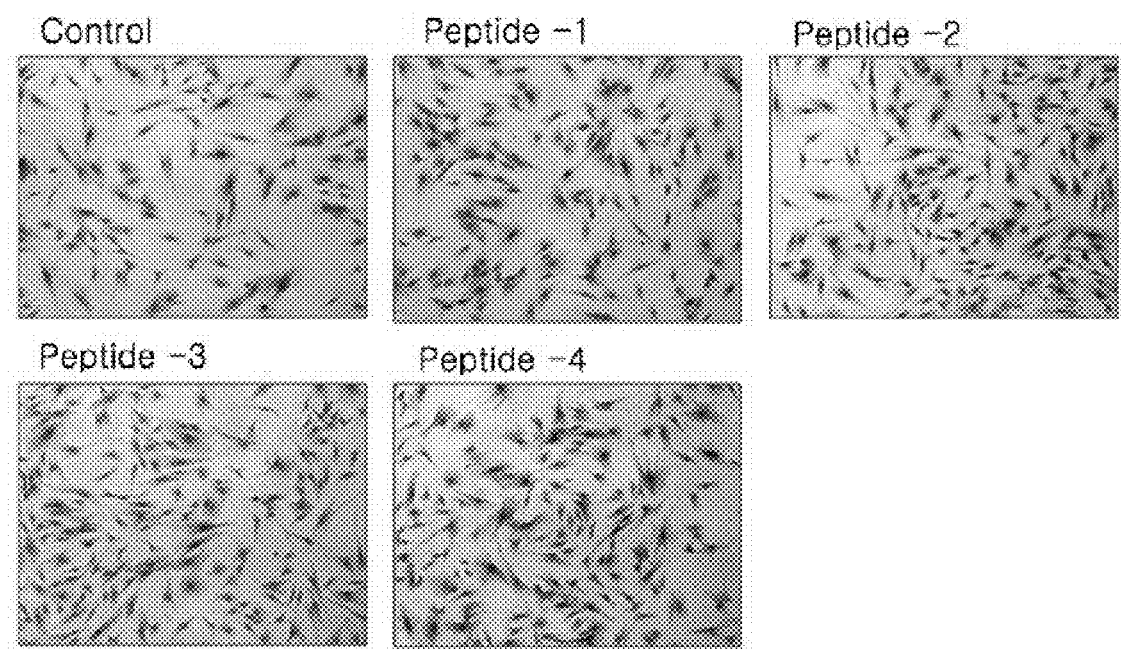
FIG. 3b is a microscope image demonstrating effects of the peptides of the present invention [SEQ ID NO:1 (peptide-1), SEQ ID NO:2 (peptide-2), SEQ ID NO:3 (peptide-3), and SEQ ID NO:4 (peptide-4)] to promote the growth of fibroblasts.
Figure 3C:
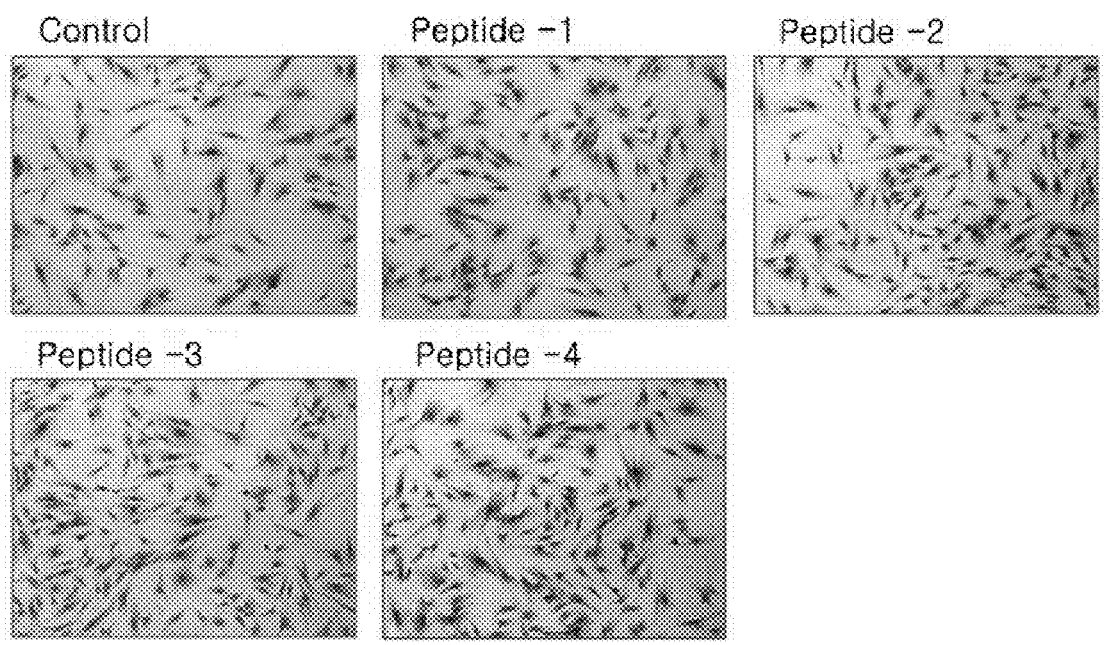
FIG. 3c is a microscope image demonstrating effects of the peptides of the present invention [SEQ ID NO:1 (peptide-1), SEQ ID NO:2 (peptide-2), SEQ ID NO:3 (peptide-3), and SEQ ID NO:4 (peptide-4)] to promote the growth of cells in hair follicles.

FIG. 2 demonstrates that the peptide of the present invention notably increases the growth of keratinocytes (FIG. 2a), fibroblasts (FIG. 2b) and hair follicle cells (FIG. 2c). FIG. 3 is a result representing that change of cell shape is observed under a microscope after cells were treated with the present peptide for 72 hr.

As shown in FIGS. 2 and 3, it could be appreciated that the peptides of the present invention promote proliferation of keratinocytes, fibroblasts, and hair follicle cells, and change their morphological shapes.

Experimental Example 2

Influence of Peptides on Elevated Amount of Receptor and Signal Gene

Figure 4:
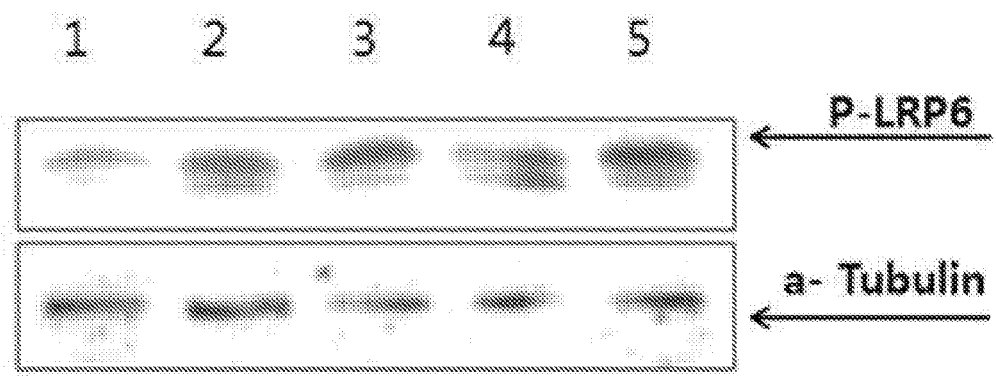
FIG. 4 is data demonstrating the enhancement of LRP5 phosphorylation by the treatment with the peptides of the present invention [SEQ ID NO:1 (peptide-1), SEQ ID NO:2 (peptide-2), SEQ ID NO:3 (peptide-3), and SEQ ID NO:4 (peptide-4)].
Figure 5A:
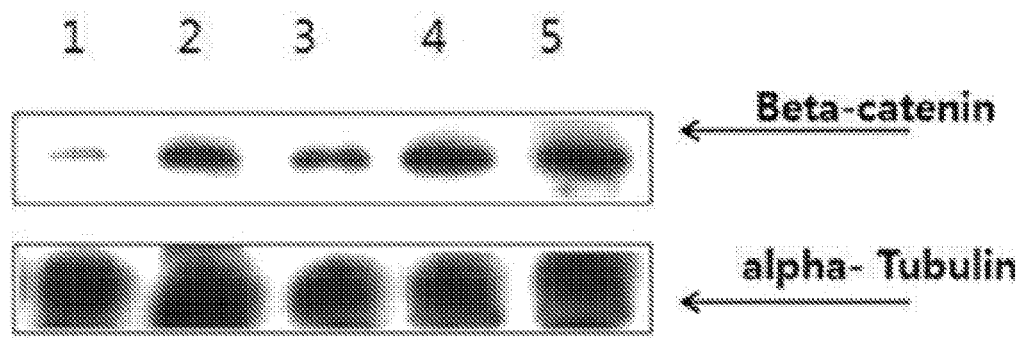
FIG. 5a is data demonstrating the enhancement of β-catenin activity by the treatment with the peptides of the present invention [SEQ ID NO:1 (peptide-1), SEQ ID NO:2 (peptide-2), SEQ ID NO:3 (peptide-3), and SEQ ID NO:4 (peptide-4)].
Figure 5B:
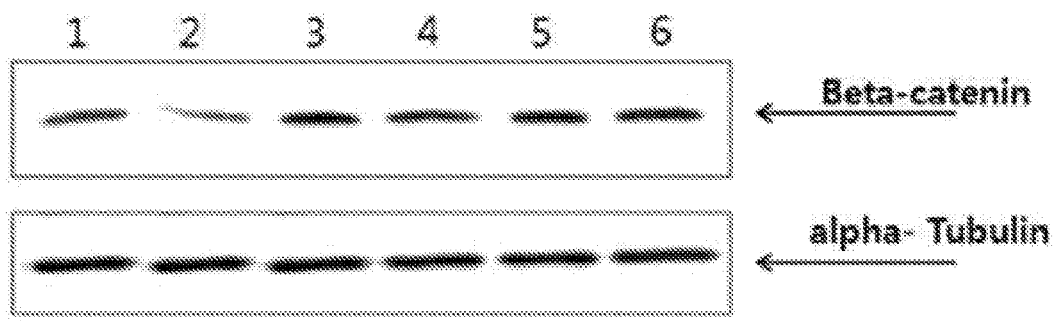
FIG. 5b is a Western blotting analysis representing the β-catenin expression in spite of the presence of DKK-1 (a WNT inhibitor and hair loss gene) by the treatment with the peptides of the present invention [SEQ ID NO:1 (peptide-1), SEQ ID NO:2 (peptide-2), SEQ ID NO:3 (peptide-3), and SEQ ID NO:4 (peptide-4)].
Figure 6:
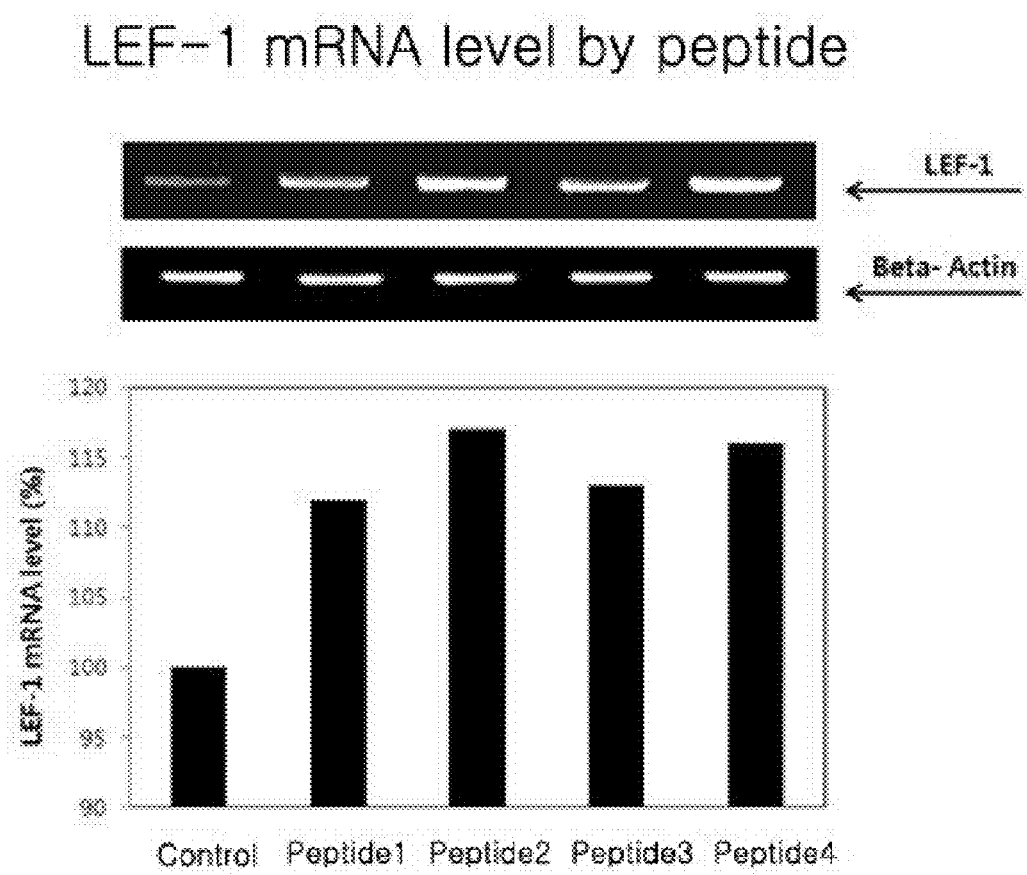
FIG. 6 is data representing the activity of LEF-1 transcription factor by the treatment with the peptides of the present invention [SEQ ID NO:1 (peptide-1), SEQ ID NO:2 (peptide-2), SEQ ID NO:3 (peptide-3), and SEQ ID NO:4 (peptide-4)].

HaCaT kerationcytes cultured for 48 hr were incubated with the peptides synthesized in preparation Example 1 for 5 hr. The phosphorylation level of LRP5, which is the receptor of WNT protein and expression level of β-catenin, which is the signal molecule of WNT protein were examined respectively. The amount of Phopho-LRP5 and β-catenin were measured by Western blot analysis using an antibody against Phopho-LRP5 (Cell signaling) and β-catenin (SantaCruz, USA). In addition, the expression level of LEF-1 transcription factor was also observed, which is enhanced by β-catenin. The peptide of the present invention significantly elevated the phosphorylation level of LRP5 (FIG. 4) and also significantly enhanced the expression level of β-catenin (FIG. 5a). First of all, it was shown that β-catenin activity is observed by treatment with the peptide of the present invention in spite of the presence of DKK-1 as a WNT inhibitor and a β-catenin signaling inhibitor (FIG. 5b). It was also observed that the expression level of LEF-1 transcription factor was increased by the treatment of the present peptides (FIG. 6).

Taken together in results of experimental Examples 1 and 2, it could be appreciated that the peptides of the present invention exerts excellent effects on promotion of hair growth and inhibition of hair loss, and also has an anti-aging activity.

Experimental Example 3

Influence of Peptides on Production of Fibronectin

To verify whether the peptides synthesized in preparation Example 1 enhances the expression of fibronectin as a WNT target protein, NIH3T3 fibroblasts ($4\times10^3$ cells) was added to each well of 96-well plates and cultured under 5% $CO_2$ for 24 hr at 37° C. After 24-hr culture, the medium was changed with a fresh medium without serum and cells were treated with empty sample (for normalization), three peptides synthesized (1 μg/ml) and peptide complex (1 μg/ml) aseptically dissolved in 10% DMSO for 3 hr, 10 hr, 24 hr or 48 hr under the same conditions as described above. After 72 hr incubation, the cell culture was collected and the expression level of fibronectin was measured using Fibronectin ELISA kit (R&D systems, USA).

Figure 7A:
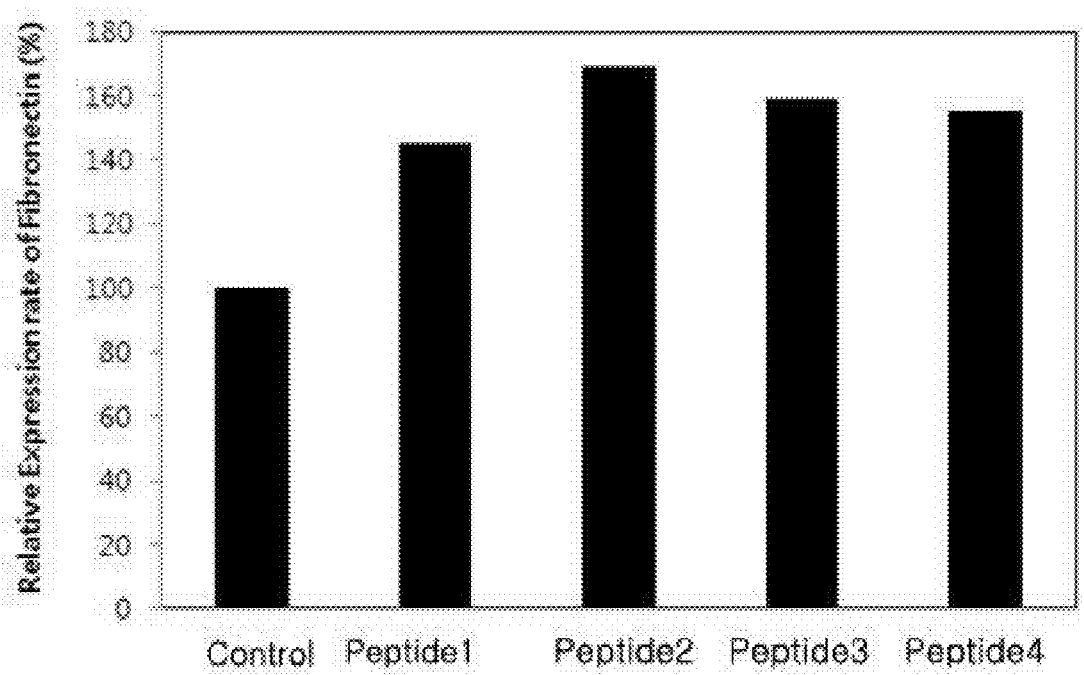
FIG. 7a is a graph representing that fibronectin expression is gradually elevated by the treatment with the peptides of the present invention [SEQ ID NO:1 (peptide-1), SEQ ID NO:2 (peptide-2), SEQ ID NO:3 (peptide-3), and SEQ ID NO:4 (peptide-4)] with the lapse of time.
Figure 7B:
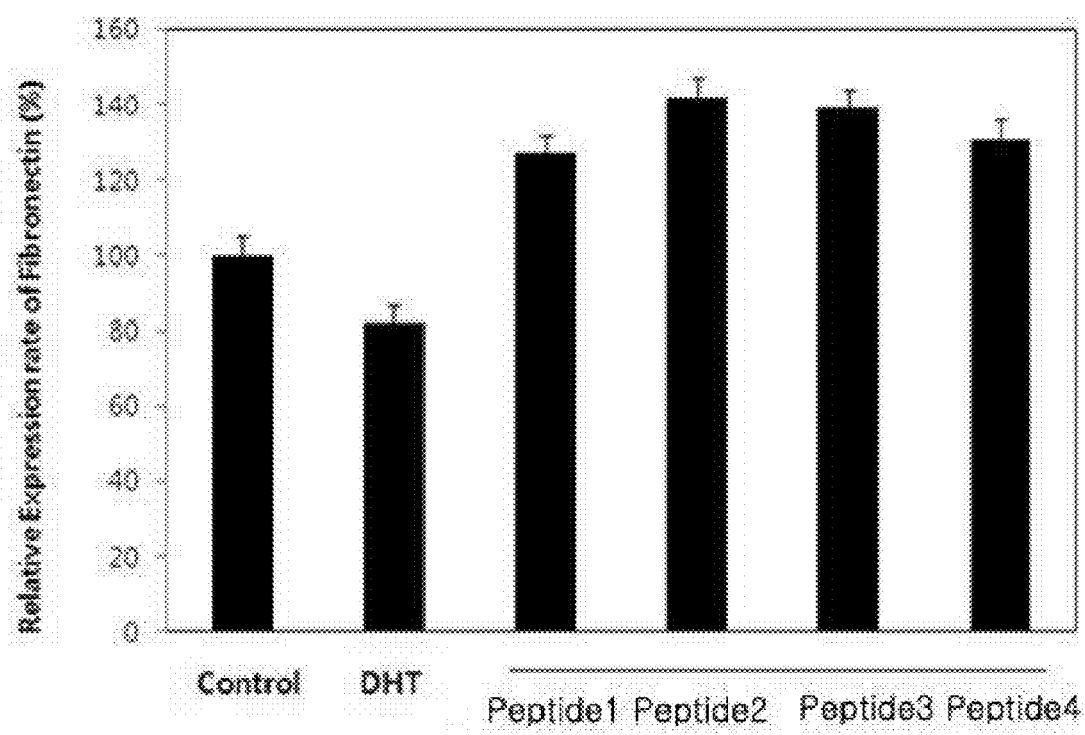
FIG. 7b represents a graph measuring changes of fibronectin expression by the present peptide. It was shown that the expression of fibronectin inhibited by DKK-1 (a WNT inhibitor and hair loss gene) was restored and enhanced by addition of the peptides of the present invention [SEQ ID NO:1 (peptide-1), SEQ ID NO:2 (peptide-2), SEQ ID NO:3 (peptide-3), and SEQ ID NO:4 (peptide-4)].

As demonstrated in FIG. 7a, the peptides of the present invention were revealed to elevate the level of fibronectin in fibroblasts with the lapse of time. In addition, after DKK-1 protein was treated and cultured under the same conditions, the expression level of fibronectin was examined. As shown in FIG. 7b, the expression level of fibronectin was restored and enhanced even in treatment with both DKK-1 protein and the present peptide.

Figure 7C:
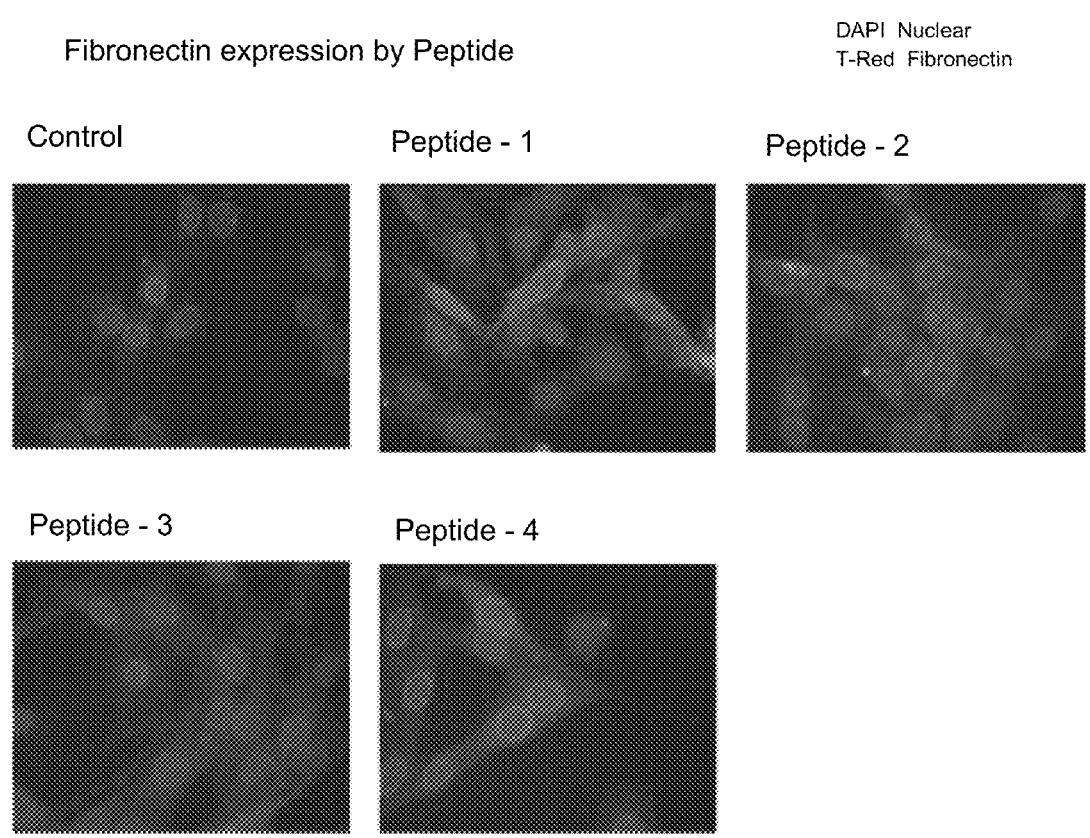
FIG. 7c is an immunostaining image representing the presence of the peptide in cells when treated with the peptides of the present invention [SEQ ID NO:1 (peptide-1), SEQ ID NO:2 (peptide-2), SEQ ID NO:3 (peptide-3), and SEQ ID NO:4 (peptide-4)].

FIG. 7c is an immunostaining image representing the presence of the peptide in cells when fibroblasts were treated with the peptides of this invention, and the existence of the present peptides in cells was demonstrated by the staining of the peptides.

Taken together, these results demonstrate that the peptides of the present invention induces WNT-β-catenin signaling pathway despite the presence of DKK-1 protein known to a WNT inhibitor and hair loss gene, contributing to promotion of hair growth, inhibition of hair loss and anti-aging.

Experimental Example 4

Analysis of Effects of Peptides on Mouse Hair Growth

Figure 8:
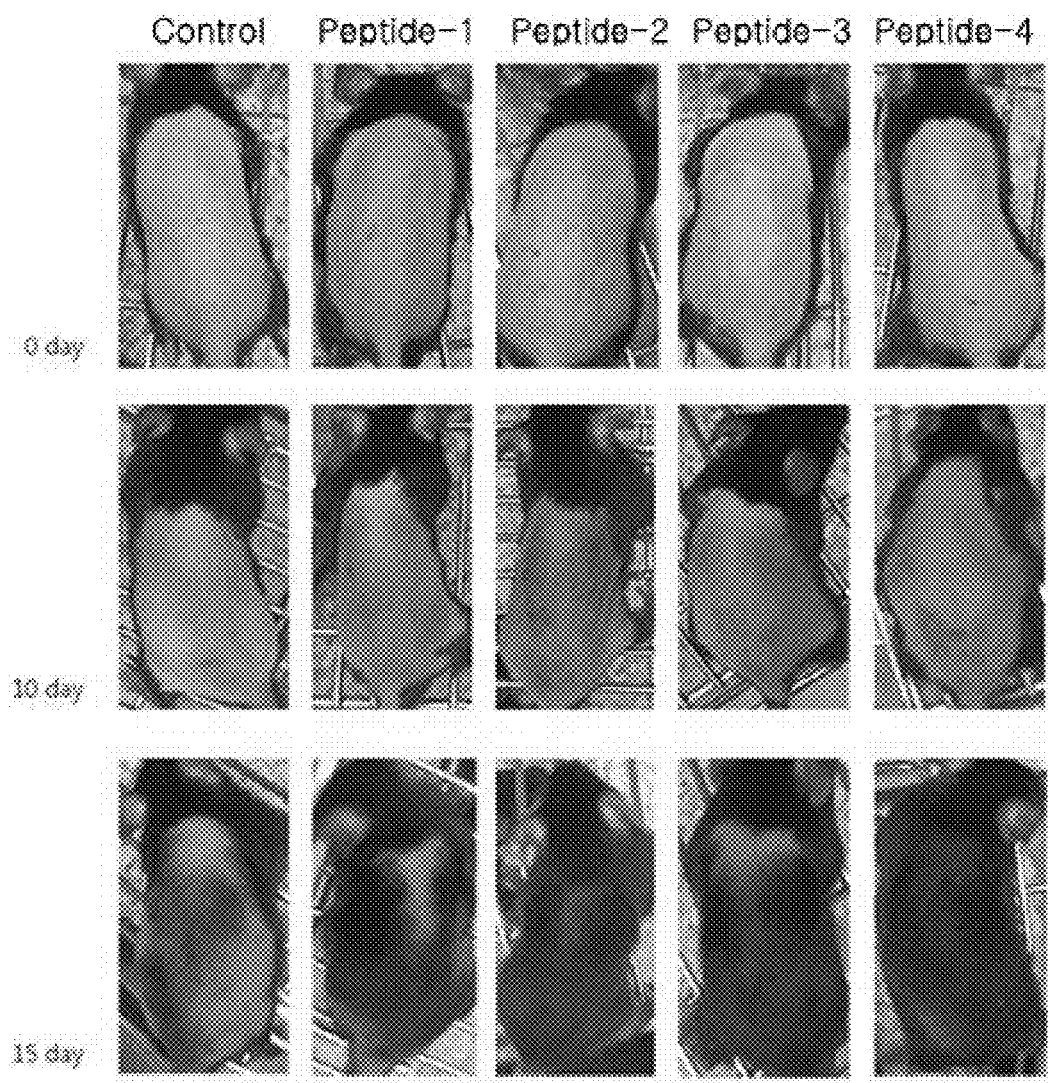
FIG. 8 represents that the peptide of the present invention [SEQ ID NO:1 (peptide-1), SEQ ID NO:2 (peptide-2), SEQ ID NO:3 (peptide-3), and SEQ ID NO:4 (peptide-4)] has an activity for promoting hair growth on mouse back skin.

The peptide synthesized in Preparation Example 1 was formulated into nanosome. Afterwards, the back of C57BL/6 mouse was partially removed and then the skin was topically administered with the nanosome twice every day for 15 days. At 10 days-treatment, growing hair was observed in mouse back skin, and the amount of hair in mouse back skin were much significantly enhanced at 15 days-treatment compared with a control group (FIG. 8).

Example 1

Preparation of Nano Peptides 50 mg of each peptide synthesized in preparation Examples was dissolved in 500 ml of distilled water by sufficient agitation. The peptide solution was mixed with 5 g lecithin, 0.3 ml sodium oleate, 50 ml ethanol and a small amount of oils, and its volume was adjusted with distilled water to 1 L. The resulting solution was subjected to a microfluidizer under high pressure for emulsification, thereby providing nanosomes having about 100-nm size. The nanosomes were prepared to have a final concentration of about 50 ppm and used as ingredients for cosmetics.

Formulation Example 1

Skin Softener

A skin softener comprising peptide-containing nanosomes prepared in Example 1 was formulated according to the following composition:

TABLE 2

| Ingredients | Content (wt %) |
|---|---|
| Peptide nanosome | 2.5 |
| 1,3-butylene glycol | 6.0 |
| Glycerin | 4.0 |
| PEG 1500 | 1.0 |
| Sodium hyaluronate | 1.0 |
| Polysorbate 20 | 0.5 |
| Ethanol | 8.0 |
| Preservative, pigment | Proper amount |

TABLE 2-continued

| Ingredients | Content (wt %) |
| --- | --- |
| Benzophenone-9 | 0.05 |
| Perfume | Minute amount |
| Distilled water | Residual amount |
| Total | 100 |

Formulation Example 2

Nutrient Cream

A nutrient cream comprising peptide-containing nanosomes prepared in Example 1 was formulated according to the following composition:

TABLE 3

| Ingredients | Content (wt %) |
| --- | --- |
| Peptide nanosome | 2.5 |
| Meadowfoam oil | 3.0 |
| Cetearylalcohol | 1.5 |
| Stearic acid | 1.5 |
| Glyceryl stearate | 1.5 |
| Liquid paraffin | 10.0 |
| Wax | 2.0 |
| Polysorbate 60 | 0.6 |
| Sorbitan sesquiolate | 2.5 |
| Squalane | 3.0 |
| 1,3-butylene glycol | 3.0 |
| Glycerin | 5.0 |
| Triethanol amine | 0.5 |
| Tocopheryl acetate | 0.5 |
| Preservative, pigments | Proper amount |
| Perfume | Proper amount |
| Distilled water | Residual amount |
| Total | 100 |

Formulation Example 3

Nutrient Liquid

A nutrient liquid comprising peptide-containing nanosomes prepared in Example 1 was formulated according to the following composition:

TABLE 4

| Ingredients | Content (wt %) |
| --- | --- |
| Peptide nanosome | 2.5 |
| 1,3-butylene glycol | 4.0 |
| Glycerin | 4.0 |
| Cetearyl alcohol | 0.8 |
| Glyceryl stearate | 1.0 |
| Triethanol amine | 0.13 |
| Tocopheryl acetate | 0.3 |
| Liquid paraffin | 5.0 |
| Squalane | 3.0 |
| Makadamianut oil | 2.0 |
| Polysorbate 60 | 1.5 |
| Sorbitan sesquiolate | 0.5 |
| Carboxyvinyl polymer | 1.0 |
| Preservative, pigments | Proper amount |
| Perfume | Proper amount |
| Distilled water | Residual amount |
| Total | 100 |

Formulation Example 4

Essence

An essence comprising peptide-containing nanosomes prepared in Example 1 was formulated according to the following composition:

TABLE 5

| Ingredients | Content (wt %) |
| --- | --- |
| Peptide nanosome | 2.5 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Formulation Example 5

Hair Serum

A hair serum comprising peptide-containing nanosomes prepared in Example 1 was formulated according to the following composition:

TABLE 6

| Ingredients | Content (wt %) |
| --- | --- |
| Peptide nanosome | 1 |
| Glycerin | 10.0 |
| 1,3-butylene glycol | 5.0 |
| PEG 1500 | 2.0 |
| Allantoin | 0.1 |
| DL-panthenol | 0.3 |
| EDTA-2Na | 0.02 |
| Hydroxyethyl cellulose | 0.1 |
| Sodium hyaluronate | 8.0 |
| Carboxyvinyl polymer | 0.2 |
| Triethanol amine | 0.18 |
| Octyldodeceth-16 | 0.4 |
| Ethanol | 6.0 |
| Perfume, preservative, pigments | Proper amount |
| Distilled water | Residual amount |
| Total | 100 |

Formulation Example 6

Hair Toner

A hair toner comprising peptide-containing nanosomes prepared in Example 1 was formulated according to the following composition:

TABLE 6

| Ingredients | Content (wt %) |
| --- | --- |
| Peptide nanosome | 1 |
| Glycerin | 2.0 |
| 1,3-butylene glycol | 2.0 |
| PEG 1500 | 2.0 |
| Allantoin | 0.1 |
| DL-panthenol | 0.3 |
| EDTA-2Na | 0.02 |
| Sodium hyaluronate | 8.0 |
| Carboxyvinyl polymer | 0.2 |
| Triethanol amine | 0.18 |
| Octyldodeceth-16 | 0.4 |
| Ethanol | 10.0 |
| Perfume, preservative, pigments | Proper amount |
| Distilled water | Residual amount |
| Total | 100 |

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A peptide having a Wingless-type mouse mammary tumor virus integration site family (WNT) protein activity and an amino acid sequence consisting of the amino acid sequence of SEQ ID NO:1, SEQ ID NO:2, SEQ ID NO:3, or SEQ ID NO:4.

2. The peptide according to claim 1, wherein the peptide has at its N-terminal a protection group selected from the group consisting of acetyl group, fluorenyl methoxy carbonyl group, formyl group, palmitoyl group, myristyl group, stearyl group and polyethylene glycol (PEG).

3. The peptide according to claim 1, wherein the peptide is derived from a human WNT protein.

4. The peptide according to claim 1, wherein the peptide facilitates cell proliferation in fibroblasts, kerationcytes or hair follicle cells.

5. The peptide according to claim 1, wherein the peptide promotes β-catenin signaling.

6. The peptide according to claim 1, wherein the peptide promotes β-catenin signaling in spite of the presence of DKK-1 (Dickkopf-1) protein, which is involved in a hair loss process.

7. The peptide according to claim 1, wherein the peptide promotes the expression of fibronectin, which is a target of WNT protein and important for hair growth.

8. A method for promoting hair growth or improving hair production comprising administering to a subject the peptide according to claim 1.

9. A method for improving hair loss comprising administering to a subject the peptide according to claim 1.

10. A method for improving skin conditions comprising administering to a subject the peptide according to claim 1.

11. The method according to claim 10, wherein the improvement in the skin condition is improvement in wrinkle or skin elasticity, of improving skin aging, improvement in skin moisture, removal of wound or regeneration of skin.

* * * * *